(12) United States Patent
Key et al.

(10) Patent No.: US 6,278,035 B1
(45) Date of Patent: Aug. 21, 2001

(54) PROCESS FOR $C_2$ RECOVERY

(76) Inventors: Ronald D. Key; William G. Brown, both of 8522 E. 61st St., Tulsa, OK (US) 74133

( * ) Notice: Subject to any disclaimer, the term of this patent is extended or adjusted under 35 U.S.C. 154(b) by 0 days.

(21) Appl. No.: 09/527,175

(22) Filed: Mar. 17, 2000

(51) Int. Cl.[7] .............................. C07C 7/00; C10G 3/00; B01D 3/00
(52) U.S. Cl. .................. 585/800; 585/802; 208/348; 208/351; 208/354; 208/355; 208/356; 62/24; 62/29; 62/31
(58) Field of Search .................... 585/800, 802; 208/348, 351, 354, 355, 356; 62/29, 24, 31

(56) References Cited

U.S. PATENT DOCUMENTS 4,895,584 * 1/1990 Buck et al. .................. 62/29

* cited by examiner

Primary Examiner—Walter D. Griffin
Assistant Examiner—Tam M. Nguyen
(74) Attorney, Agent, or Firm—William S. Dorman

(57) ABSTRACT

An improved process for separating a hydrocarbon bearing feed gas containing methane and lighter, $C_2$ (ethylene and/or ethane), and heavier components into a fraction containing predominantly methane and lighter components and a fraction containing predominantly $C_2$ and heavier hydrocarbon components including the steps of cooling and partially condensing and delivering the feed stream to a separator to provide a first residue vapor and a first liquid containing $C_2$, directing a first part of the first liquid containing $C_2$ into a heavy-ends fractionation column wherein the liquid is separated into a second hydrocarbon bearing vapor residue and a second liquid product containing $C_2$; further cooling the second part of the first liquid containing $C_2$ and partially condensing the second hydrocarbon bearing vapor residue; combining the cooled second part of the first liquid and partially condensed second hydrocarbon-bearing vapor residue and directing them to a second separator effecting a third residue and a third liquid; cooling and directing a first part of the third liquid into the lights-ends fractionation column, to thereby condense $C_2$'s and heavier components while the methane is evaporated in the light-ends fractionation column to thereby obtain fourth residue vapor and liquid, heating and supplying the fourth liquid recovered from the light-ends fractionation column to the heavy-ends fractionation column as a feed thereto; conducting the second part of the third liquid to the heavy-ends fractionation column as a feed thereto.

5 Claims, 2 Drawing Sheets

PROCESS FOR $C_2$ RECOVERY

BACKGROUND OF THE INVENTION

1. Field of the Invention

This invention relates to an improved process for separating a hydrocarbon-bearing feed gas which contains methane and lighter components, (not necessarily all hydrocarbon components), $C_2$ (ethylene and ethane), and heavier hydrocarbon components into two fractions. The first fraction contains predominantly methane and lighter components and the second fraction contains the recovered desirable $C_2$ and heavier components. More particularly, this invention relates to a process and apparatus wherein the yield of $C_2$'s is increased or alternatively energy consumption is reduced for a given $C_2$ recovery.

2. The Prior Art

Hydrocarbon-bearing gas may contain lighter components (e.g., hydrogen, nitrogen, etc.) methane, ethane, and/or ethylene, and a substantial quantity of hydrocarbons of higher molecular weight, for example, propane, butane, pentane and often their unsaturated analogs. Recent changes in ethylene/ethane demand have created increased markets for ethylene/ethane and have created a need for more efficient processes which yield higher recovery levels of this product. In more recent times, the use of cryogenic processes utilizing the principle of gas expansion through a mechanical device to produce power while simultaneously extracting heat from the system have been employed. The use of such equipment depends upon the pressure of the gas source, the composition of the gas and the desired end results. In the typical cryogenic expansion-type recovery processes used in the prior art, a gas stream under pressure is cooled by heat exchange with other streams of the process and/or external sources of cooling are employed such as refrigeration systems. As the gas is cooled, liquid is condensed and is collected and separated so as to thereby obtain desired hydrocarbons. The high-pressure liquid feed is typically transferred to a demethanizer column after the pressure is adjusted to the operating pressure of the demethanizer. In such fractionation column the liquid feed is fractionated to separate the residual methane and lighter components from the desired products of ethylene/ethane and heavier hydrocarbon components. In the ideal operation of such separation processes, the vapor leaving the process contain substantially all of the methane and lighter components found in the feed gas and substantially no ethylene/ethane or heavier hydrocarbon components remain. The bottom fraction leaving the demethanizer typically contains substantially all of the ethylene/ethane and heavier hydrocarbon components with very little methane or lighter components which is discharged in the fluid gas outlet from the demethanizer.

A patentability search was conducted on the present invention and the following references were uncovered.

| Inventor | U.S. Pat. No. | Issue Date |
|---|---|---|
| Harandi | 4,664,784 | 5/12/1987 |
| Buck et al | 4,895,584 | 1123/1990 |
| Campbell et al | 5,771,712 | 9/01/1998 |
| Wilkinson et al | 5,699,507 | 6/30/1998 |

U.S. Pat. No. 4,664,784—Issued May 12, 1987

M. N. Harandi to Mobil Oil Corporation

In a reference directed to fractionation of hydrocarbon mixtures, teachings are found on column 4, line 32 et sequitur re: a zone (81) wherein a descending liquid heavy-ends portion contacts an ascending vaporous light-ends portion so as ". . . to aid in heat transfer between vapor and liquid." (column 4, line 44).

U.S. Pat. No. 4,895,584—Issued Jan. 23, 1990

L. L. Buck et al to Pro-Quip Corporation

A reference that claims an improved process for hydrocarbon separation and teaches supplying of the liquid recovered from the light-ends fractionation column to the heavy-ends fractionation column and directing part of the ($C_2$ containing) liquid from a first step into intimate contact with a second residue, which liquid provides additional liquefied methane which acts with the partially condensed second residue as a direct contact refrigerant to thereby condense $C_2$ and heavier comprising hydrocarbons while methane itself is evaporated in the light-ends fractionation column.

On column 1, lines 56–67 the following teachings are found: ". . . feed gas is first cooled and partially condensed and delivered to a separator to provide a first residue vapor and a liquid containing $C_2$ . . . Part of the liquid containing $C_2$ from the separator may be directed into a heavy-ends fractionation column wherein the liquid is separated into a second residue containing lighter hydrocarbons and $C_2$ containing products. A part of the first residue vapors with at least part of the partially condensed second residue are counter currently contacted and commingled in a light-ends fractionation column (emphasis added) . . . "

On column 2, lines 1–10 the following teachings are found: "The liquids recovered from the light-ends fractionation column are then fed to the heavy-ends fractionation column as a liquid feed. A portion of the liquids containing $C_2$ from the separator is fed into intimate contact with the second residue prior to discharging the commingled liquids and gases into the light-ends fractionation column to thereby achieve mass and heat transfer (emphasis added) to thereby liquefy a higher percent of the $C_2$ and heavier hydrocarbon components while the methane is vaporized" (column 2, lines 1–10).

The following Elcor Corporation references describe the recovery of $C_3$ and heavier hydrocarbons via processes wherein counter-current contact of a stream drawn from a deethanizer with a stream in a separator/absorber takes place:

U.S. Pat. No. 5,799,507—Issued Sep. 1, 1998

J. D. Wilkinson et al to Elcor Corporation

See column 4, line 2 re: ". . . liquid portion of expanded stream commingles with liquids falling downward from the absorbing section . . . " l.o.w., the stream (36) from the deethanizer (17) flows through heat exchanger (20) to become stream (36a) which flows into the upper section of separator (15) where it ". . . contacts the vapors rising upward through the absorption section" (column 5, lines 3–4).

U.S. Pat. No. 5,771,712—Issued Jun. 30, 1998

R. E. Campbell et al to Elcor Corporation

This reference teaches essentially the same as Wilkinson et al.

None of the foregoing patents discussed above embody the present invention.

SUMMARY OF THE INVENTION

The present invention provides processes for increasing the ethylene and ethane component of the discharge from the process unit at reduced energy consumption than the prior art. The foregoing advantage is achieved in the present invention by a process in which the feed gas is first cooled and partially condensed and delivered to a separator to provide a first residue vapor and a first liquid containing $C_2$ which liquid also contains lighter hydrocarbons. A first part of the first liquid containing $C_2$ from the separator may be directed into a heavy-ends fractionation column, wherein the liquid is separated into a second residue containing lighter hydrocarbons and a second liquid product containing $C_2$. A second part of the first liquid from the separator is cooled. The second residue is cooled and partially condensed and then combined with the cooled second part of the first liquid providing, upon separation, a third residue and a third liquid. A first part of the third liquid is cooled and fed to the light-ends fractionation column. A second part of the third liquid is fed directly to the heavy-ends fractionation column. A part of the first residue vapor with a cooled first part of the third liquid are counter-currently contacted and commingled in a light-ends fractionation column to thereby provide fourth residue vapor and liquid which are separately discharged. Cooling the first part of the third liquid prior to its introduction into the light-ends fractionation column aids in mass and heat transfer. This cooling thereby provides for greater liquefaction of a higher percent of the $C_2$ and heavier hydrocarbon components while the methane contained in the first part of the third liquid is vaporized. The fourth liquid recovered from the light-ends fractionation column is heated then introduced to the heavy-ends fractionation column as a feed.

A better understanding of the invention will be had with reference to the following description and claims, taken in conjunction with the attached drawings.

DESCRIPTION OF THE PREFERRED EMBODIMENTS

The improved processes of the present disclosure include the steps of cooling a gaseous hydrocarbon-containing feed stream to form a first vapor stream and a first liquid stream. A first part of the first liquid stream is transferred to a heavy-ends fractionation column while the first vapor stream is transferred to the bottom of a light-ends fractionation column. The heavy-ends fractionation column overhead vapor, which consists mainly of methane, ethylene, and/or ethane, is cooled and partially condensed. The cooled heavy-ends fractionation column overhead is combined with a cooled second part of the first liquid stream. The resulting stream is fed to a separator and separated into a third residue vapor and a third liquid. A first part of the third liquid is cooled and fed to the upper portion of the light-ends fractionation column. The liquid flows downwardly within the light-ends fractionation column and contacts gaseous ethylene and/or ethane and heavier hydrocarbons that flow upwardly. The methane portion of the liquid stream is vaporized by absorbing heat from the gaseous ethylene/ethane and heavier hydrocarbons which causes the ethylene/ethane and heavier hydrocarbons to condense and exit at the bottom of the light-ends fractionation column. The gaseous methane and lighter components within the light-ends fractionation column are removed from the overhead as a product of the process. The second part of the third liquid may be used to reflux the heavy-ends fractionation column. The fourth liquid at the bottom of the light-ends fractionation column is removed and used to cool other process streams; the thus-heated fourth liquid is fed to the upper portion of the heavy-ends fractionation column. The liquid at the bottom of the heavy-ends fractionation column is removed as a product of the process.

Figure 1:
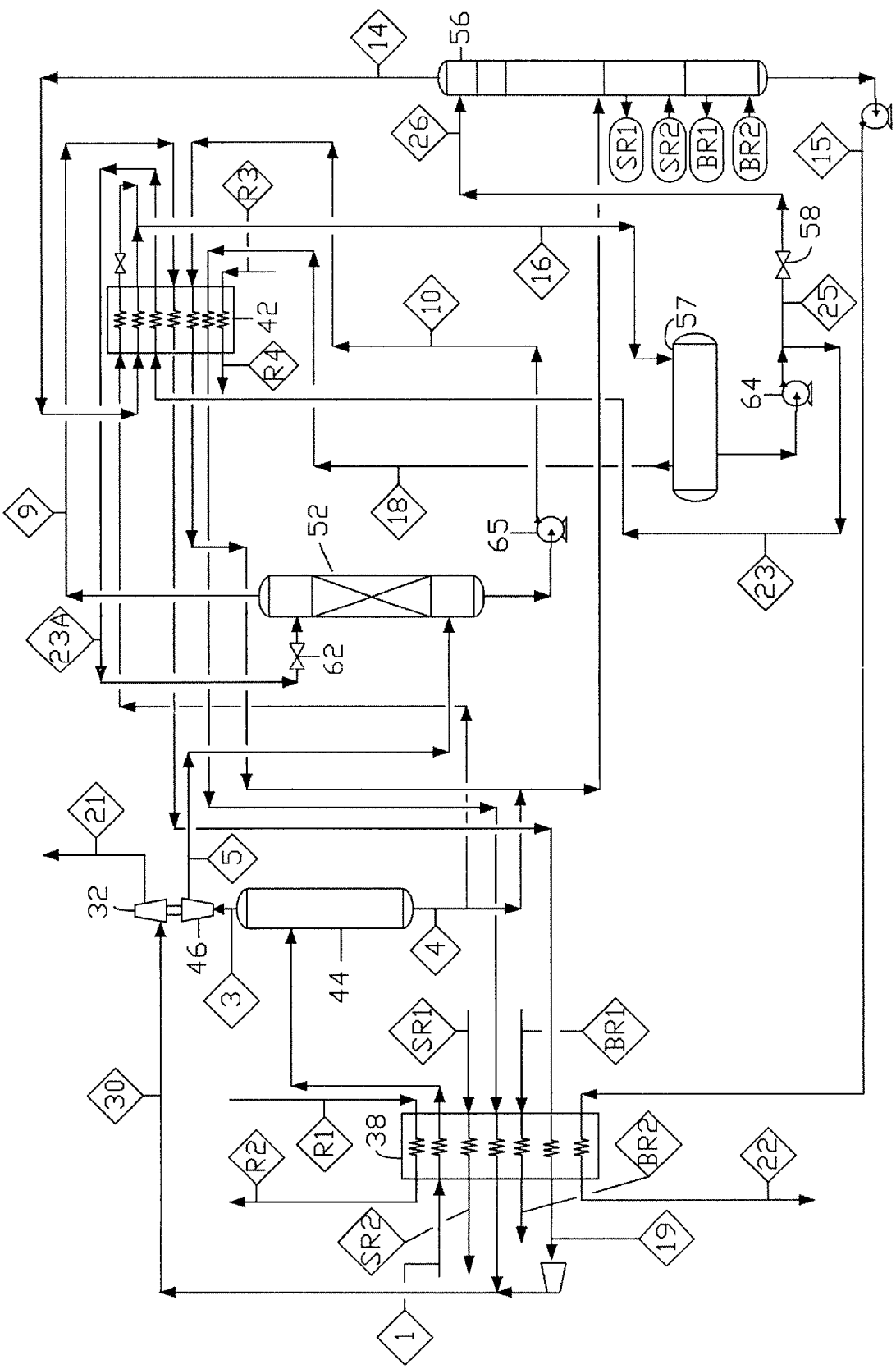
FIG. 1 is a schematic flow diagram illustrating a method of practicing a preferred embodiment of the invention.

The improved process of this invention is illustrated in a first embodiment in FIG. 1. The incoming gas stream 1 at a temperature of 120° F. and a pressure of 827 psia passes through heat exchanger 38, so that the temperature thereof is reduced to about −72° F. with attendant partial condensation. Pressure is reduced as the gas flows through the heat exchangers resulting in a pressure of 812 psia at −72° F. at which the raw gas is delivered into a separator 44. Within separator 44 the cooled gas stream is separated into a first liquid stream (stream 4) and a first residue vapor, stream 3. Stream 3 is passed through a turbo expander 46. The shaft of turbo expander 46 is connected directly to the shaft of the booster compressor 32. From the turbo expander, the first residue gas having a temperature of about −163° F. at 200 psia passes by way of stream 5 into a light-ends fractionation column 52.

From separator 44 a first part of the first liquid containing $C_2$ is conducted into a heavy-ends fractionation column 56 by way of stream 4A. A second part of the first liquid containing $C_2$ from stream 4 is channeled by way of stream 4B through heat exchanger 42 where its temperature is decreased. The cooled liquid exits the heat exchanger and combines with the cooled residue stream 14 to form stream 16.

The second residue from heavy-ends fractionation column 56, having a temperature of about −132° F., is fed by way of stream 14 through heat exchanger 42, combines with the remainder of the liquid containing $C_2$ from stream 4B above, and by way of stream 16 into the reflux separator 57. A first part of the third liquid from the reflux separator 57 is routed by stream 23 through heat exchanger 42 where its temperature is reduced. This liquid stream is then passed as stream 23A into the light-ends fractionation column 52. The liquid from stream 23A passes downwardly through the light-ends fractionation column 52 and encounters the rising first residue gas from stream 5 so that mass and latent heat transfer occur. The second part of the third liquid from the reflux separator 57 is routed by stream 26 to the heavy-ends fractionation column 56.

The light-ends fractionation column 52 functions as a combination heat and mass transfer device. The column has two feed streams; that is, streams 5 and 23A, and two product streams; that is, streams 10 and 9. The light-ends fractionation column 52 consists of at least one, and preferably more, theoretical liquid-vapor equilibrium stages.

Vapor enters the light-ends fractionation column by way of stream 5 as a bottom feed while the top feed is by way of stream 23A which is a liquid enriched by condensed methane. The methane and lighter constituents and un-recovered ethylene and ethane, exit as a dew point vapor as a fourth residue (stream 9) from the top tray or separation stage of the light-ends fractionation column 52.

The top feed through stream 23A into the light-ends fractionation column 52 and particularly the methane content thereof serves as a reflux in the column. In flowing from stage to stage within column 52, the liquid methane is vaporized and in turn the liquid is progressively enriched in ethylene and ethane condensed from the upflowing bottom feed vapor from stream 5.

The fourth liquid stream from the light-ends fractionation column 52, stream 10, provides process cooling in exchanger 42 while it is itself warmed and then fed to the heavy-ends fractionation column 56 for further separation.

The fourth residue gas (stream 9) discharged from light-ends fractionation column 52 passes through exchangers 42 and 38 and exits the heat exchanger system as stream 19. The third residue gas vapor in stream 18 exiting the reflux separator 57 also pass through exchangers 42 and 38 and exit the heat exchanger system as stream 28. The warmed vapor from the light-ends fractionation column (stream 19) is compressed in compressor 48 to the same pressure as stream 28 and combined with stream 28 to form stream 30. The combined vapors of stream 30 are compressed in the booster compressor 32. At this stage, the methane rich off-gas in stream 21 has a temperature of 103° F. and a pressure of 187 psia. If it is desired to return the discharge gas to the same system from which the raw gas was taken, such as for further transportation of the gas, the pressure will need to be raised back to that substantially equal to the incoming pressure of 827 psia in stream 1.

The second liquid discharge, rich in $C_2$ content, from the lower end of the heavy-ends fractionation column 56 is passed by way of stream 15 and exchanger 38 to product discharge stream 22.

The result of a simulation of the process of FIG. 1 is set forth in Table 1A wherein the moles per hour of various constituents of the streams are set forth. The process achieves a recovery of about 97.37 percent of the $C_2$ content of the feed gas in addition to substantially complete recovery of the $C_3$ and heavier hydrocarbon components of the feed gas stream into the less volatile fraction (product).

Table 1B relates the moles per hour of various constituents of the stream of the process of FIG. 1 when the process of FIG. 1 is applied to a feed gas stream that is enriched in ethane and heavier components.

Figure 2:
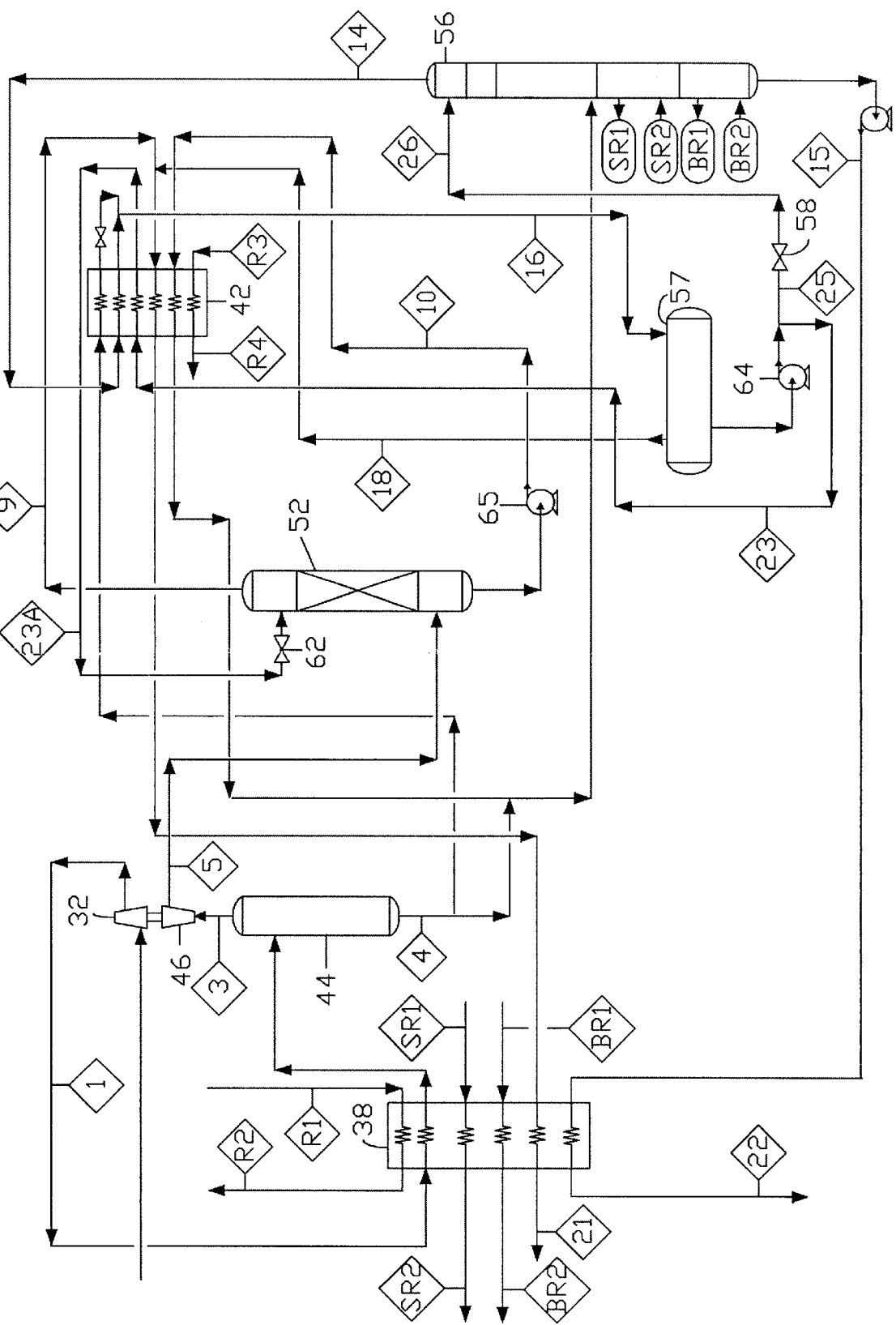
FIG. 2 is a schematic flow diagram illustrating a variation in the preferred embodiment of the present invention.

FIG. 2 shows an alternate embodiment of the invention. The components of the process of FIG. 2 having the same basic structure and function of those of the system of FIG. 1 are given like numbers. The process is as described with reference to FIG. 1, except that the booster compressor 32 is placed on the feed gas (stream 1) and streams 9 and 18 are combined prior to exchanger 42.

Table 2, shows the result of a simulation of the system of FIG. 2. Table 2 provides the moles per hour of various constituents for the various streams of this embodiment of the process. The process achieves a recovery of about 91.64 percent of the ethylene and 96.77 percent of the ethane content of the feed gas in addition to substantially complete recovery of the $C_3$ and heavier hydrocarbon components of the feed gas stream in to the less volatile fraction (product).

The process has been illustrated using various standard components employed for the sequence of treating steps with it being understood that the process may be practiced utilizing different physical apparatus. For instance, the turbo expander can, in many instances, be eliminated or replaced by a Joule-Thomson isenthalpic control valve. The difference is that where the expander is eliminated or where the Joule-Thomson valve is substituted for the turbo expander, normally greater inlet and refrigeration compression duties are required.

A different arrangement has been shown in the alternate embodiment for cooling the second residue effluent and thus providing reflux to the light-ends fractionation and heavy-ends fractionation columns.

Some of the processes in each instance may use multiple turbo expanders. The desirability of the use of multiple turbo expanders is predicated primarily upon the amount of hydrogen content of the inlet gas in stream 1. It is understood that, according to the inlet gas content, only single turbo expanders may be employed in practicing the process; or, in some instances as previously indicated, turbo expanders may be eliminated completely or substituted by one or more Joule-Thomson isenthalpic expansion valves.

An important feature of the process is the employment of the light-ends fractionation column 52 which functions as a combination heat and mass transfer device. The use of the reflux in the top stage means that the liquid methane of the reflux is vaporized; and in turn the liquid is progressively enriched in ethylene and ethane condensed from the upflowing bottom feed vapor to thereby recover a higher percent of the $C_2$ components.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

TABLE 1A

THE PRO-QUIP CORPORATION

| STREAM NAME | STREAM NUMBER | | | | | | | | | |
|---|---|---|---|---|---|---|---|---|---|---|
| | 1 | 3 | 4 | 5 | 9 | 10 | 14 | 16 | 18 | 23 |
| NITROGEN | 99.17 | 93.86 | 5.31 | 93.86 | 92.74 | 2.50 | 7.81 | 7.81 | 6.43 | 1.38 |
| CARBON DIOXIDE | 8.64 | 6.19 | 2.45 | 6.19 | 1.89 | 5.83 | 1.95 | 1.95 | 0.42 | 1.53 |
| METHANE | 7552.91 | 6526.79 | 1026.12 | 6526.79 | 6374.89 | 1115.68 | 2131.34 | 2131.34 | 1168.58 | 963.78 |
| ETHANE | 486.41 | 272.65 | 213.76 | 272.65 | 9.22 | 299.03 | 39.18 | 39.18 | 3.57 | 35.60 |
| PROPANE | 198.31 | 56.60 | 141.71 | 56.60 | 0.04 | 58.45 | 1.92 | 1.92 | 0.03 | 1.89 |
| I-BUTANE | 36.66 | 5.59 | 31.07 | 5.59 | 0.00 | 5.67 | 0.08 | 0.08 | 0.00 | 0.08 |
| N-BUTANE | 63.30 | 7.19 | 56.11 | 7.19 | 0.00 | 7.27 | 0.08 | 0.08 | 0.00 | 0.08 |
| I-PENTANE | 20.83 | 1.16 | 19.67 | 1.16 | 0.00 | 1.17 | 0.01 | 0.01 | 0.00 | 0.01 |
| N-PENTANE | 20.63 | 0.86 | 19.77 | 0.86 | 0.00 | 0.86 | 0.00 | 0.00 | 0.00 | 0.00 |
| HEXANE | 19.29 | 0.29 | 19.00 | 0.29 | 0.00 | 0.29 | 0.00 | 0.00 | 0.00 | 0.00 |
| TOTAL LBMOL/HR | 8525.10 | 6971.27 | 1553.83 | 6971.27 | 6478.78 | 1496.83 | 2182.36 | 2182.36 | 1179.02 | 1004.35 |
| MASS FLOW LB/HR | 160249 | 119227 | 41022 | 119227 | 105232 | 30726 | 35770 | 35770 | 19055 | 16732 |

TABLE 1A-continued

THE PRO-QUIP CORPORATION

| | | | | | | | | | | |
|---|---|---|---|---|---|---|---|---|---|---|
| VOLUME FLOW MMSCFD | 78 | 63 | — | — | 59 | — | 20 | — | 11 | — |
| MOLE. WT. | 18.80 | 17.10 | 26.40 | 17.10 | 16.24 | 20.53 | 16.39 | 16.39 | 16.16 | 16.66 |
| DENSITY LB/FT$^3$ | 2.83 | 5.92 | 26.30 | 1.51 | 1.32 | 26.94 | 2.06 | 4.01 | 2.35 | 20.51 |
| TEMPERATURE ° F. | 120 | −72 | −72 | −163 | −178 | −165 | −132 | −153 | −153 | −153 |
| PRESSURE PSIA | 827.00 | 812.00 | 812.00 | 200.00 | 193.00 | 385.00 | 330.00 | 328.00 | 328.00 | 353.00 |

| STREAM NAME | STREAM NUMBER | | | | | Percent Recovered to Volatile Fraction | Percent Recovered to Less Volatile Fraction |
|---|---|---|---|---|---|---|---|
| | 25 | 26 | 15 | 22 | 21 | | |
| NITROGEN | 0.00 | 0.00 | 0.00 | 0.00 | 99.17 | 100.00% | 0.00% |
| CARBON DIOXIDE | 0.00 | 0.00 | 6.33 | 6.33 | 2.31 | 26.71% | 73.30% |
| METHANE | 0.00 | 0.00 | 10.46 | 10.46 | 7543.46 | 99.87% | 0.14% |
| ETHANE | 0.00 | 0.00 | 473.61 | 473.61 | 12.79 | 2.63% | 97.37% |
| PROPANE | 0.00 | 0.00 | 198.24 | 198.24 | 0.07 | 0.04% | 99.96% |
| I-BUTANE | 0.00 | 0.00 | 36.66 | 36.66 | 0.00 | 0.00% | 100.00% |
| N-BUTANE | 0.00 | 0.00 | 63.30 | 63.30 | 0.00 | 0.00% | 100.00% |
| I-PENTANE | 0.00 | 0.00 | 20.83 | 20.83 | 0.00 | 0.00% | 100.00% |
| N-PENTANE | 0.00 | 0.00 | 20.63 | 20.63 | 0.00 | 0.00% | 100.00% |
| HEXANE | 0.00 | 0.00 | 19.29 | 19.29 | 0.00 | 0.00% | 100.00% |
| | | | | | | | |
| TOTAL LBMOL/HR | 0.00 | 0.00 | 868.31 | 868.31 | 7657.80 | | |
| MASS FLOW LB/HR | 0 | 0 | 35978 | 35978 | 124286 | | |
| VOLUME FLOW MMSCFD | — | — | — | — | 70 | | |
| MOLE. WT. | 16.66 | 16.66 | 41.44 | 41.44 | 16.23 | | |
| DENSITY LB/FT$^3$ | 20.51 | 20.51 | 30.11 | 27.97 | 1.03 | | |
| TEMPERATURE ° F. | −153 | −153 | 71 | 100 | 167 | | |
| PRESSURE PSIA | 353.00 | 353.00 | 500.00 | 495.00 | 413.41 | | |

TABLE 1B

THE PRO-QUIP CORPORATION

| STREAM NAME | STREAM NUMBER | | | | | | | | | |
|---|---|---|---|---|---|---|---|---|---|---|
| | 1 | 3 | 4 | 5 | 9 | 10 | 14 | 16 | 18 | 23 |
| NITROGEN | 345.88 | 280.87 | 65.02 | 280.87 | 275.89 | 16.91 | 19.90 | 84.91 | 69.99 | 11.93 |
| CARBON DIOXIDE | 327.77 | 161.06 | 166.70 | 161.06 | 48.44 | 254.24 | 37.16 | 203.85 | 26.83 | 141.62 |
| METHANE | 24864.18 | 16379.96 | 8484.21 | 16379.96 | 17115.17 | 6530.39 | 8271.66 | 16754.42 | 7672.43 | 7265.60 |
| ETHANE | 3696.03 | 1309.26 | 2386.76 | 1309.26 | 179.47 | 3053.40 | 131.47 | 2518.25 | 113.74 | 1923.61 |
| PROPANE | 2012.72 | 363.60 | 1649.12 | 363.60 | 10.96 | 1673.25 | 11.09 | 1660.25 | 9.49 | 1320.61 |
| I-BUTANE | 385.41 | 40.55 | 344.87 | 40.55 | 0.43 | 316.09 | 0.54 | 345.41 | 0.46 | 275.96 |
| N-BUTANE | 612.71 | 50.73 | 561.98 | 50.73 | 0.35 | 500.03 | 0.49 | 562.47 | 0.41 | 449.65 |
| I-PENTANE | 151.53 | 7.05 | 144.48 | 7.05 | 0.02 | 122.62 | 0.03 | 144.51 | 0.03 | 115.59 |
| N-PENTANE | 115.29 | 4.29 | 111.00 | 4.29 | 0.01 | 93.09 | 0.01 | 111.02 | 0.01 | 88.80 |
| HEXANE | 98.82 | 1.67 | 97.15 | 1.67 | 0.00 | 79.39 | 0.00 | 97.15 | 0.00 | 77.72 |
| HYDROGEN SULFIDE | 0.00 | 0.00 | 0.00 | 0.00 | 0.00 | 0.00 | 0.00 | 0.00 | 0.00 | 0.00 |
| CARBONYL SULFIDE | 3.29 | 0.68 | 2.61 | 0.68 | 0.03 | 2.74 | 0.03 | 2.64 | 0.03 | 2.09 |
| | | | | | | | | | | |
| TOTAL LBMOL/HR | 32613.64 | 18599.74 | 14013.90 | 18599.74 | 17630.77 | 12642.15 | 8472.40 | 22484.88 | 7893.41 | 11673.17 |
| MASS FLOW LB/HR | 708883 | 339451 | 369432 | 339451 | 290366 | 352036 | 139402 | 508812 | 130123 | 302951 |
| VOLUME FLOW MMSCFD | 297 | 169 | — | — | 161 | — | 77 | — | 72 | — |
| MOLE. WT. | 21.74 | 18.25 | 26.36 | 18.25 | 16.47 | 27.85 | 16.45 | 22.63 | 16.48 | 25.95 |
| DENSITY LB/FT$^3$ | 4.20 | 6.88 | 24.02 | 1.76 | 1.46 | 32.32 | 2.07 | 6.70 | 2.06 | 30.02 |
| TEMPERATURE ° F. | 120 | −40 | −40 | −133 | −149 | −138 | −129 | −131 | −131 | −131 |
| PRESSURE PSIA | 978.00 | 966.35 | 966.35 | 242.00 | 237.00 | 375.00 | 335.00 | 330.00 | 330.00 | 370.00 |

| STREAM NAME | STREAM NUMBER | | | | | Percent Recovered to Volatile Fraction | Percent Recovered to Less Volatile Fraction |
|---|---|---|---|---|---|---|---|
| | 25 | 26 | 15 | 22 | 21 | | |
| NITROGEN | 2.98 | 2.98 | 0.00 | 0.00 | 345.88 | 100.00% | 0.00% |
| CARBON DIOXIDE | 35.40 | 35.40 | 252.48 | 252.48 | 75.27 | 22.97% | 77.03% |
| METHANE | 1816.40 | 1816.40 | 75.13 | 75.13 | 24787.60 | 99.69% | 0.30% |
| ETHANE | 480.90 | 480.90 | 3402.83 | 3402.83 | 293.21 | 7.93% | 92.07% |
| PROPANE | 330.15 | 330.15 | 1992.30 | 1992.30 | 20.46 | 1.02% | 98.99% |
| I-BUTANE | 68.99 | 68.99 | 384.53 | 384.53 | 0.89 | 0.23% | 99.77% |
| N-BUTANE | 112.41 | 112.41 | 611.95 | 611.95 | 0.76 | 0.12% | 99.88% |
| I-PENTANE | 28.90 | 28.90 | 151.49 | 151.49 | 0.04 | 0.03% | 99.97% |
| N-PENTANE | 22.20 | 22.20 | 115.28 | 115.28 | 0.02 | 0.02% | 99.98% |
| HEXANE | 19.43 | 19.43 | 98.82 | 98.82 | 0.00 | 0.00% | 00.00% |

TABLE 1B-continued

THE PRO-QUIP CORPORATION

|  |  |  |  |  |  |  |  |
|---|---|---|---|---|---|---|---|
| HYDROGEN SULFIDE | 0.00 | 0.00 | 0.00 | 0.00 | 0.00 | 0.00% | 00.00% |
| CARBONYL SULFIDE | 0.52 | 0.52 | 3.23 | 3.23 | 0.06 | 1.84% | 98.16% |
| TOTAL LBMOL/HR | 2918.29 | 2918.29 | 7088.04 | 7088.04 | 25524.18 | | |
| MASS FLOW LB/HR | 75738 | 75738 | 288372 | 288372 | 420489 | | |
| VOLUME FLOW MMSCFD | — | — | — | — | 232 | | |
| MOLE. WT. | 25.95 | 25.95 | 40.68 | 40.68 | 16.47 | | |
| DENSITY LB/FT$^3$ | 30.02 | 30.02 | 30.09 | 27.83 | 0.88 | | |
| TEMPERATURE °F. | −131 | −131 | 72 | 100 | 115 | | |
| PRESSURE PSIA | 370.00 | 370.00 | 500.00 | 490.00 | 317.14 | | |

TABLE 2

THE PRO-QUIP CORPORATION

| STREAM NAME | STREAM NUMBER | | | | | | | | | |
|---|---|---|---|---|---|---|---|---|---|---|
| | 1 | 3 | 4 | 5 | 9 | 10 | 14 | 16 | 18 | 23 |
| HYDROGEN | 1274.20 | 1203.16 | 71.03 | 1203.16 | 1200.28 | 3.85 | 29.12 | 75.29 | 73.92 | 0.96 |
| NITROGEN | 197.10 | 165.03 | 32.07 | 165.03 | 162.81 | 5.39 | 17.96 | 38.80 | 34.30 | 3.16 |
| CARBON MONOXIDE | 13.01 | 10.54 | 2.47 | 10.54 | 10.36 | 0.52 | 1.53 | 3.13 | 2.65 | 0.34 |
| METHANE | 3194.56 | 1790.74 | 1403.81 | 1790.74 | 1992.70 | 641.30 | 1485.42 | 2397.90 | 1197.69 | 843.29 |
| ETHYLENE | 672.81 | 127.55 | 545.26 | 127.55 | 29.42 | 356.01 | 39.41 | 393.82 | 26.82 | 257.87 |
| ETHANE | 1402.52 | 155.95 | 1246.57 | 155.95 | 21.51 | 711.58 | 34.92 | 845.19 | 23.80 | 577.13 |
| PROPENE | 195.47 | 5.89 | 189.58 | 5.89 | 0.24 | 92.39 | 0.64 | 123.86 | 0.41 | 86.74 |
| PROPANE | 156.55 | 3.57 | 152.98 | 3.57 | 0.12 | 73.40 | 0.35 | 99.79 | 0.22 | 69.96 |
| I-BUTANE | 1.51 | 0.01 | 1.50 | 0.01 | 0.00 | 0.70 | 0.00 | 0.98 | 0.00 | 0.68 |
| N-BUTANE | 81.73 | 0.45 | 81.28 | 0.45 | 0.00 | 37.57 | 0.02 | 52.86 | 0.01 | 37.13 |
| N-PENTANE | 28.36 | 0.03 | 28.33 | 0.03 | 0.00 | 12.97 | 0.00 | 18.42 | 0.00 | 12.94 |
| TOTAL LBMOL/HR | 7217.81 | 3462.92 | 3754.89 | 3462.92 | 3417.45 | 1935.67 | 1609.35 | 4050.03 | 1359.84 | 1890.19 |
| MASS FLOW LB/HR | 142766 | 44774 | 97992 | 44774 | 40727 | 52131 | 26634 | 90329 | 21895 | 48083 |
| VOLUME FLOW MMSCFD | 66 | 32 | — | — | 31 | — | 15 | — | 12 | — |
| MOLE. WT. | 19.78 | 12.93 | 26.10 | 12.93 | 11.92 | 26.93 | 16.55 | 22.30 | 16.10 | 25.44 |
| DENSITY LB/FT$^3$ | 2.13 | 2.82 | 28.62 | 0.71 | 0.63 | 33.86 | 1.07 | 3.84 | 1.03 | 31.33 |
| TEMPERATURE °F. | 100 | −89 | −89 | −171 | −183 | −175 | −146 | −152 | −152 | −152 |
| PRESSURE PSIA | 581.00 | 726.00 | 726.00 | 148.60 | 145.00 | 213.00 | 185.00 | 181.00 | 181.00 | 213.00 |

| STREAM NAME | STREAM NUMBER | | | | | Percent Recovered to Volatile Fraction | Percent Recovered to Less Volatile Fraction |
|---|---|---|---|---|---|---|---|
| | 25 | 26 | 15 | 22 | 21 | | |
| HYDROGEN | 0.41 | 0.41 | 0.00 | 0.00 | 1274.20 | 100.00% | 0.00% |
| NITROGEN | 1.34 | 1.34 | 0.00 | 0.00 | 197.11 | 100.00% | 0.00% |
| CARBON MONOXIDE | 0.14 | 0.14 | 0.00 | 0.00 | 13.01 | 100.00% | 0.00% |
| METHANE | 356.91 | 356.90 | 4.21 | 4.21 | 3190.39 | 99.87% | 0.13% |
| ETHYLENE | 109.14 | 109.14 | 616.58 | 616.58 | 56.24 | 8.36% | 91.64% |
| ETHANE | 244.26 | 244.27 | 1357.22 | 1357.22 | 45.32 | 3.23% | 96.77% |
| PROPENE | 36.71 | 36.71 | 194.82 | 194.82 | 0.65 | 0.33% | 99.67% |
| PROPANE | 29.61 | 29.61 | 156.21 | 156.21 | 0.34 | 0.22% | 99.78% |
| I-BUTANE | 0.29 | 0.29 | 1.51 | 1.51 | 0.00 | 0.00% | 99.97% |
| N-BUTANE | 15.71 | 15.71 | 81.71 | 81.71 | 0.02 | 0.02% | 99.98% |
| N-PENTANE | 5.48 | 5.48 | 28.36 | 28.36 | 0.00 | 0.00% | 100.00% |
| TOTAL LBMOL/HR | 800.00 | 800.00 | 2440.62 | 2440.62 | 4777.28 | | |
| MASS FLOW LB/HR | 20351 | 20351 | 80146 | 80146 | 62622 | | |
| VOLUME FLOW MMSCFD | — | — | — | — | | | |
| MOLE. WT. | 25.44 | 25.44 | 32.84 | 32.84 | | | |
| DENSITY LB/FT$^3$ | 31.33 | 31.33 | 30.51 | 23.64 | | | |
| TEMPERATURE °F. | −152 | −152 | −7 | 74 | | | |
| PRESSURE PSIA | 213.00 | 213.00 | 585.00 | 580.00 | | | |

We claim:

1. In a process for separation of a gas stream containing methane, $C_2$ and heavier hydrocarbon components into a volatile residue gas fraction and a relatively less volatile fraction containing said $C_2$ components and heavier hydrocarbon components, in which process;

(a) the feed gas is cooled in one or more heat exchangers and then directed to a separator providing thereby a first residue vapor and a first liquid which contains $C_2$ and other lighter and heavier hydrocarbons; and (b) a first part of the first liquid containing $C_2$ is directed into a heavy-ends fractionation column wherein said liquid is separated into a second residue containing lighter hydrocarbons and a liquid product containing $C_2$;

the improvements comprising;

(1) cooling said second residue to partially condense it;
(2) cooling a second part of said first liquid containing $C_2$ from (b) and combining the same with said partially condensed second residue stream from (1) resulting in a third liquid stream and a third residue vapor;
(3) dividing said third liquid produced in step (2) into first and second parts;
(4) further cooling said first part of said third liquid;
(5) directing said second part of the third liquid to the heavy-ends fractionation column;
(6) intimately contacting at least part of said first residue vapor with said cooled first part of third liquid from step (4) in at least one contacting stage and thereafter separating a fourth residue vapor and fourth liquid containing $C_2$ from said contacting device;
(7) supplying the fourth liquid thereby recovered in step (6) above to a heat exchanger for heating the same and thereafter into the heavy-ends fractionation column as a feed thereto;
(8) recovering as product the combined third residue vapor and the fourth residue vapor;
(9) recovering as product the second liquid stream from the heavy-ends fractionation column.

2. The improvement according to claim 1 wherein said contacting step (6) is carried out in a light-ends fractionation column that includes fractionation means for vapor/liquid counter-current contact and;

(i) wherein said cooled first part of the third liquid is introduced into said light end fractionation column above said fractionation means, whereby the cooled first part of the third liquid passes downwardly through said fractionation means;

(ii) supplying at least part of the first residue vapor to said light-ends fractionation column below said fractionation means, whereby the first residue vapor rises through said fractionation means in counter-current contact with the cooled first part of the third liquid.

3. The improvement according to claim 2 wherein the fractionation means in said light-ends fractionation column provides the equivalent of at least one theoretical liquid-vapor equilibrium stage arranged to contact at least part of said first residue vapor with the cooled first part of the third liquid stream.

4. The improvement according to claim 1 including the step of cooling the first part of the third liquid from step (3) prior to delivery of the same to the light-ends fractionation column.

5. The improvement according to claim 1 including the step of cooling the second part of the first liquid from (b) prior to combination of the second part of the first liquid with the partially condensed second residue stream from step (1) above.

* * * * *